United States Patent
Govindappa et al.

(10) Patent No.: US 9,388,227 B2
(45) Date of Patent: Jul. 12, 2016

(54) PROCESS OF EXPRESSING A FULLY FOLDED FUNCTIONAL TWO CHAIN INSULIN GLARGINE

(75) Inventors: Nagaraj Govindappa, Bangalore (IN);
Suma Sreenivas, Bangalore (IN);
Komal N. Kanojia, Bangalore (IN);
Yogesh Basavaraju, Bangalore (IN);
Kedamath Nanjund Sastry, Bangalore (IN)

(73) Assignee: Biocon Limited (IN)

( * ) Notice: Subject to any disclaimer, the term of this patent is extended or adjusted under 35 U.S.C. 154(b) by 0 days.

(21) Appl. No.: 14/388,545

(22) PCT Filed: Jun. 6, 2012

(86) PCT No.: PCT/IB2012/052853
§ 371 (c)(1),
(2), (4) Date: Sep. 26, 2014

(87) PCT Pub. No.: WO2013/144685
PCT Pub. Date: Oct. 3, 2013

(65) Prior Publication Data
US 2015/0118710 A1    Apr. 30, 2015

(30) Foreign Application Priority Data
Mar. 29, 2012  (IN) .......................... 1228/CHE/2012

(51) Int. Cl.
*C07K 14/62* (2006.01)
*A61K 38/28* (2006.01)
*C12P 21/02* (2006.01)
*C12N 15/81* (2006.01)
*C12N 9/64* (2006.01)

(52) U.S. Cl.
CPC .............. *C07K 14/62* (2013.01); *C12N 9/6454* (2013.01); *C12N 15/81* (2013.01); *C12P 21/02* (2013.01); *C12Y 304/21061* (2013.01); *Y02P 20/52* (2015.11)

(58) Field of Classification Search
CPC ...................................................... C07K 14/62
See application file for complete search history.

(56) References Cited

U.S. PATENT DOCUMENTS

| | | | |
|---|---|---|---|
| 4,929,553 A | 5/1990 | Bussey et al. | |
| 5,077,204 A | 12/1991 | Brake et al. | |
| 6,800,606 B1 | 10/2004 | You-Min et al. | |
| 2009/0197339 A1* | 8/2009 | Young | C07K 14/765 435/471 |
| 2010/0196953 A1* | 8/2010 | Geipel | C07K 14/62 435/69.1 |

FOREIGN PATENT DOCUMENTS

| | | |
|---|---|---|
| EP | 0794254 A2 | 9/1997 |
| WO | WO-2008037735 A1 | 4/2008 |
| WO | WO-2009104199 A1 | 8/2009 |
| WO | WO-2013144685 A1 | 10/2013 |

OTHER PUBLICATIONS

Hoshino et al., FEBS Letters 419: 9-12, 1997.*
"International Application Serial No. PCT/IB2012/052853, International Search Report mailed Sep. 12, 2012", 5 pgs.

* cited by examiner

*Primary Examiner* — Gyan Chandra
(74) *Attorney, Agent, or Firm* — Schwegman Lundberg & Woessner, P.A.

(57) ABSTRACT

The disclosure relates to a process of obtaining a fully folded two chain insulin glargine that require no further processing to make it functionally active. The present disclosure discloses a surprising effect of over expression of Kex2p intracellularly under the control of inducible FLD1 promoter in the host *Pichia pastoris* to produce two chain functional glargine secreted directly in the medium. The schematic diagram of how the two chains are made inside the host *Pichia pastoris* and secretes into the medium.

7 Claims, 10 Drawing Sheets

Existing Glargine sequence:

Kex2p | Trypsin cleavage sites

Mat-α KREEAEAEAEPRFVNQHLCGSHLVEALYLVCGERGFFYTPKTRRGIVEQCCTSIC
SLYQLENYCG

Two chain glargine secretion strategy:

Mat-α KRFVNQHLCGSHLVEALYLVCGERGFFYTPKTRRGIVEQCCTSICSLYQLENYCG (Kex2p cleavage site)

Lane M = Marker
Lane1 = Plasmid digested with BamH1
Lane2 = Plasmid digested with Sac1
Lane3 = Plasmid digested with Xba1
Lane4 = Plasmid digested with BamH1 & Xba1
Lane5 = PCR confirmation using gene specific primer

PROCESS OF EXPRESSING A FULLY FOLDED FUNCTIONAL TWO CHAIN INSULIN GLARGINE

PRIORITY APPLICATIONS

This application is a U.S. National Stage Filing under 35 U.S.C. 371 from International Application No. PCT/IB2012/052853, filed on 6 Jun. 2012, and published as WO2013/144685 on 3 Oct. 2013, which application claims the benefit to Indian Application No. 1228/CHE/2012, filed on 29 Mar. 2012; which applications and publication are incorporated herein by reference in their entirety.

TECHNICAL FIELD

The disclosure relates to a method of obtaining biologically active functional insulin glargine into the culture medium without the use of the proteolytic enzyme trypsin in the downstream process. More specifically, the disclosure relates to designing an expression system by co-expressing Kex2p using FLD1 promoter in Pichia pastoris to produce functional two chain glargine into the medium to enable processing of the insulin glargine into active two chain fully folded form invivo.

BACKGROUND AND PRIOR ART

Recombinant forms of glargine have been produced in various microbial expression systems, wherein organisms such as E. coli, Saccharomyces cerevisiae have been employed for the commercial production of recombinant human insulin and derivatives thereof. Owing to certain disadvantages of these systems such as low expression levels, difficulties in downstream purification etc. the use of methylotrophic yeast Pichia pastoris (P. pastoris) has been favored as a protein expression system. The expression system offers several advantages such as high expression, simple processing, low production cost, high density culture (U.S. Pat. No. 6,800,606).

Insulin Glargine is a slow acting insulin analogue. Use of E. coli as an expression system for the expression is already there in the prior art. As E. coli does not have the cellular machinery for folding the expressed polypeptide and establish the disulphide bridges correctly, so there is a need in the art to overcome such folding problem.

The glargine downstream process involves the clipping of the precursor using trypsin. Trypsin has the specificity of clipping at the carboxyl terminal of both 'K' and 'R' (as shown in fig: 1). This results in the generation of more product related impurities (as shown in fig: 1)

```
1) FVNQHLCGSHLVEALYLVCGER,
2) FVNQHLCGSHLVEALYLVCGERGFFYTPK,
3) FVNQHLCGSHLVEALYLVCGERGFFYTPKTR,
4) GFFYTPKTR
5) TRR
```

The disadvantages associated with the known downstream processes of the prior art have been remedied in the instant disclosure.

U.S. Pat. No. 4,929,553 and its related applications are concerned with the specific processing of secreted proteins in genetically modified yeast cells. Specifically, this disclosure is concerned with the use of recombinant DNA to produce Kex2 in greater quantities. The expression of proteins and use of Kex2p to processes after the cleave after dibasic amino acid is known in the prior art.

WO2008037735 and its related applications disclosed a method for making mature human insulin or an analogue wherein C-terminal amino acid residue in the B-chain cleaved off by means of a carboxypeptidase activity either within the fungi cell or subsequently in the culture medium.

Hence, there exists a need in the art to produce a process of producing a functional two chain glargine into the medium to enable processing of the insulin glargine into active two chain fully folded form invivo.

STATEMENT OF DISCLOSURE

Accordingly, the present disclosure relates to a process of expressing a fully folded functional two chain insulin glargine that require no further processing to make it functionally active, said process comprising steps of i) cloning a glargine pro-peptide and a protease in Pichia pastoris; wherein, the sequence coding for protease is put under the control of a constitutive or inducible promoter, ii) co-expressing the said pro-peptide and the protease and iii) obtaining a fully functional insulin glargine; a process of converting pro insulin glargine into fully folded biologically active insulin glargine, said method comprising steps of i) obtaining a host cell comprising a nucleotide sequence encoding pro insulin glargine, ii) co-expressing Kex2p under the control of FLD1 promoter within the host cell to convert the pro-peptide glargine into a fully folded biologically active insulin glargine.

BRIEF DESCRIPTION OF ACCOMPANYING DRAWINGS

The features of the present disclosure will become more fully apparent from the following description taken in conjunction with the accompanying drawings. Understanding that the drawings depict only several embodiments in accordance with the disclosure and are therefore, not to be considered limiting of its scope, the disclosure will be described with additional specificity and detail through use of the accompanying drawings.

Figures 5, 6:
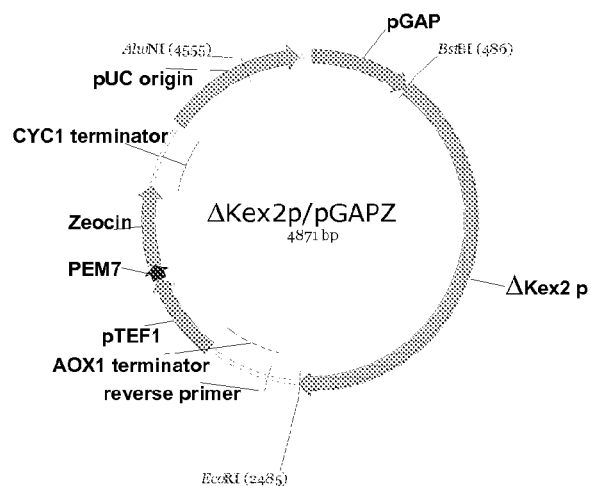

FIG. 5 illustrates and represents the single chain glargine sequence with Kex2p cleavage sites. The protease cleaves after dibasic amino acids and secretes the two chain glargine into the medium. This will not generate any other impurities.

FIG. 6 illustrates the vector map of ΔKex2p/pGAP under the control of GAP promoter intracellulary.

Figure 7:
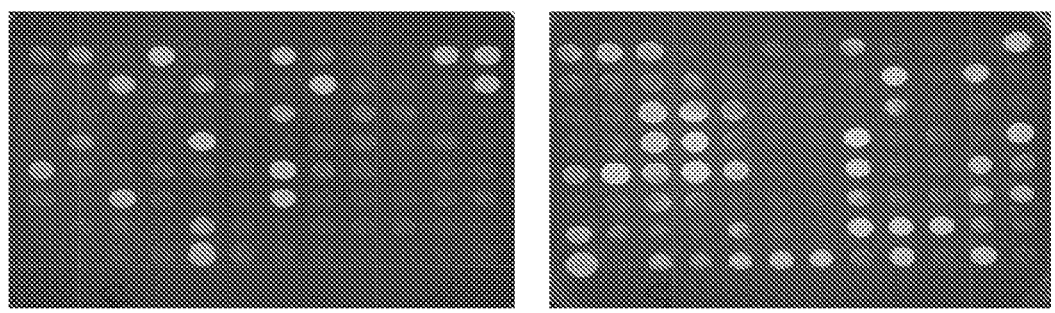

FIG. 7 illustrates the representative picture showing the resistance to Zeocin. The colonies were picked up, grown in YPD broth and stamped onto YPD plates containing 0.5 mg/ml Zeocin.

Figure 8:
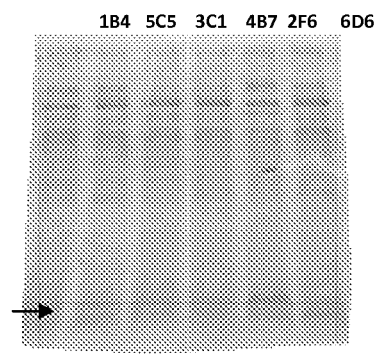
Figure 9:
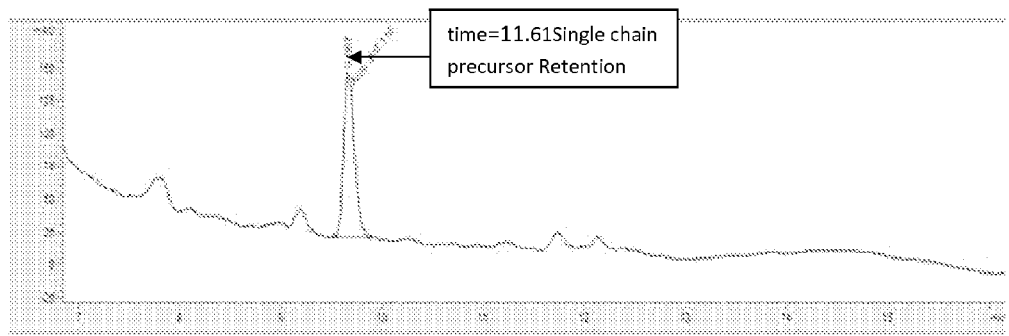

FIG. 8 illustrates that the clones were induced with methanol and secreted supernatant was analyzed using tricine SDS PAGE FIG. 9 illustrates the typical HPLC profile showing F-glargine#1 without kex2Δp660. Only precursor glargine peak obtained.

Figure 10:
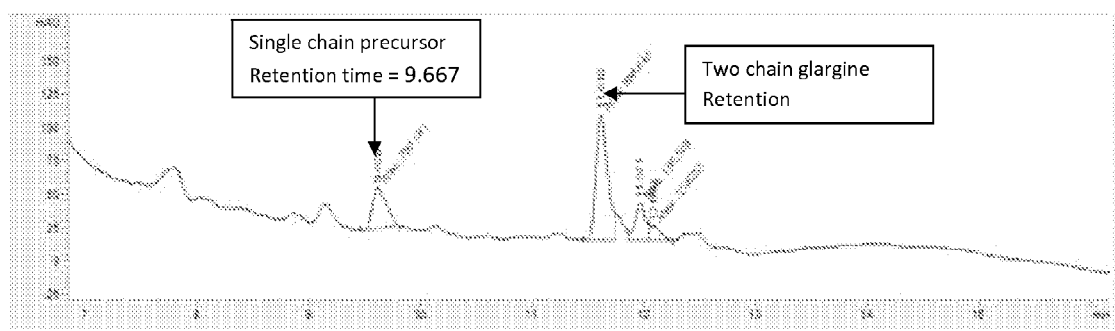

FIG. 10 illustrates the typical HPLC profile showing F-glargine expression profile with co-expression of kex2Δp660 under the control of constitutive GAP promoter. Precursor glargine peak appears at RT ~9.6 to 10 mins and processed glargine peak appears at 11.6 to 12 mins.

Figure 11:
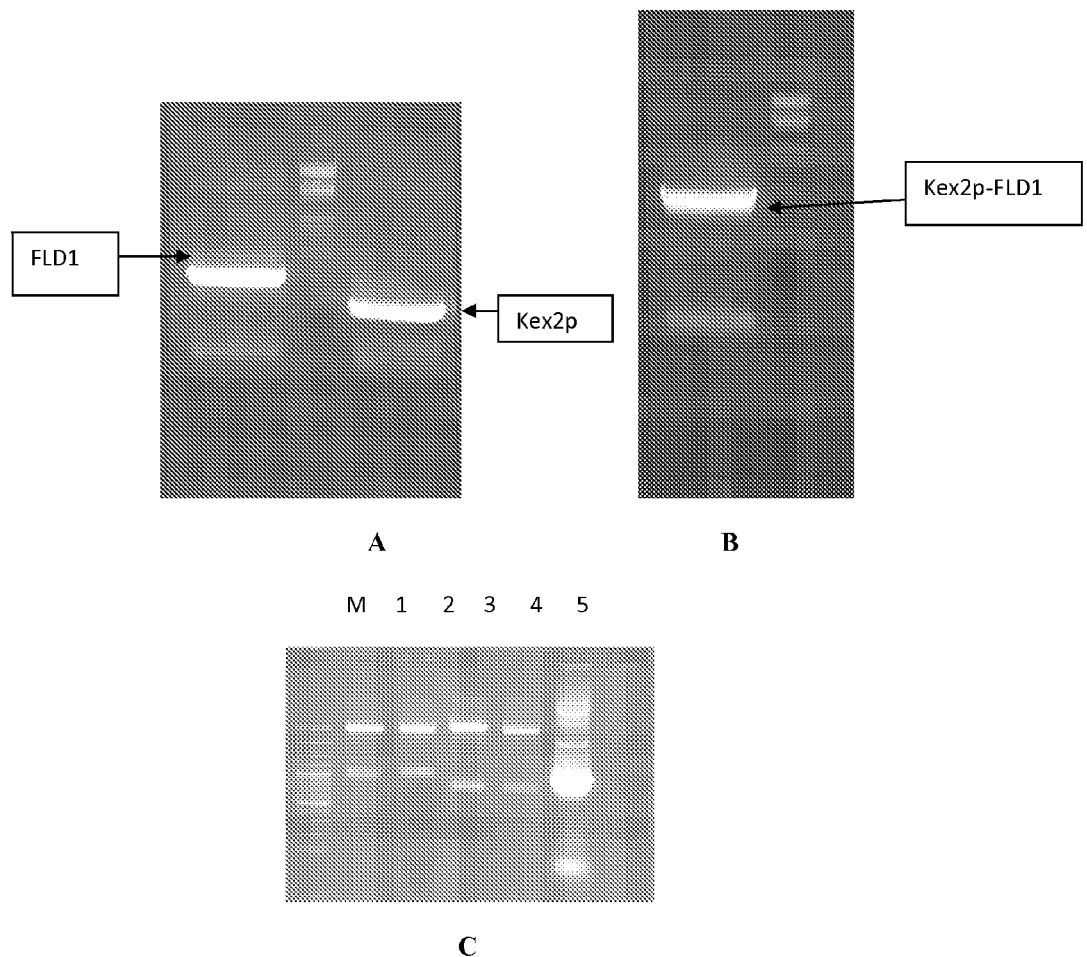
Figure 12:
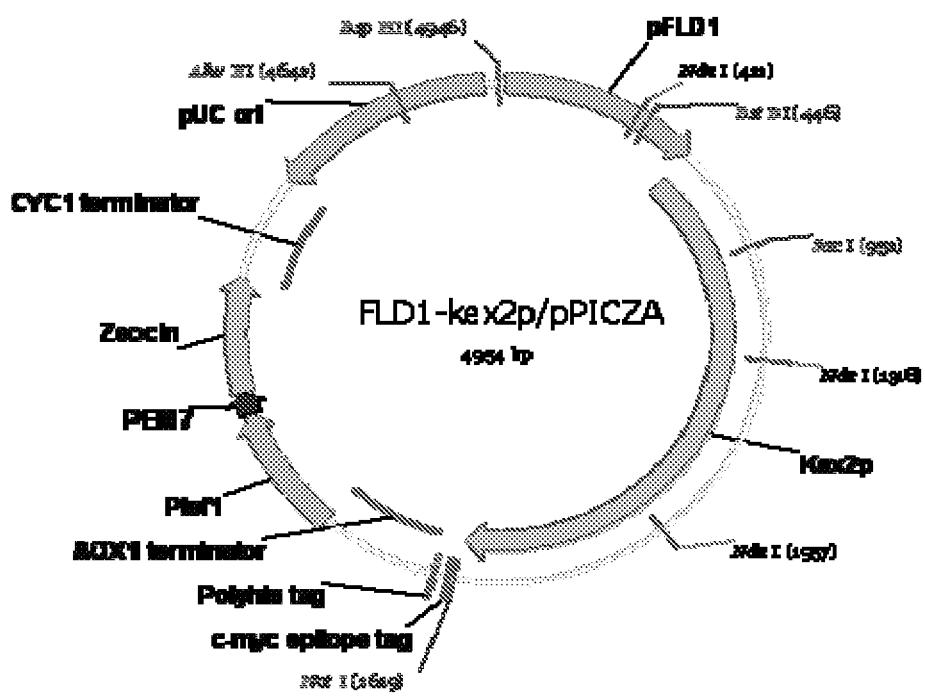
Figure 13:
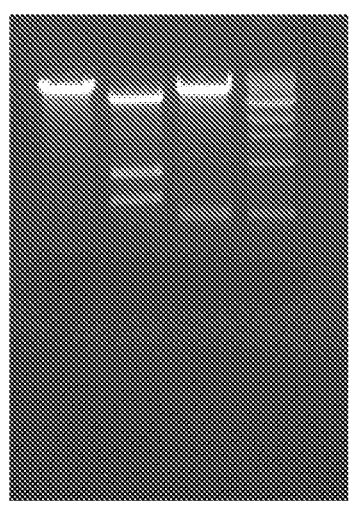

FIG. 11 illustrates the following:
A) Showing the PCR fragments amplified in separate tubes. Left side is FLD1 promoter, right side Kex2p fragment and the middle lane is the λDNA EcoRI/Hind3 marker.
B) Fused PCR product run on 1% agarose gel.
C) Restriction analysis of FLD1-ΔKex2p/pTZ57R FIG. 12 illustrates the vector map showing features of FLD1-Kex2p/pPICZA FIG. 13 illustrates the restriction analysis of FLD1-Kex2p/pPICZA: Lane1=Digestion with Pst1/EcoRV (linearizes), Lane 2=Digestion with Nde1 (Expected 639 bp, 956 bp, 3407 bp), Lane3=Digestion with BstB1 and Sac1 (Expected 511 bp, 4448 bp).

Figure 14:
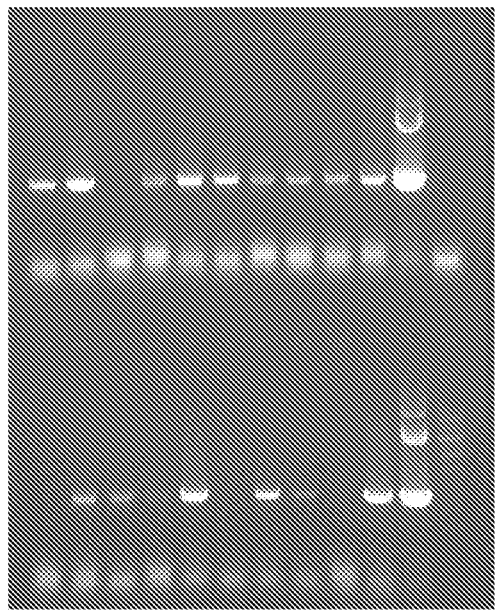
Figure 14:
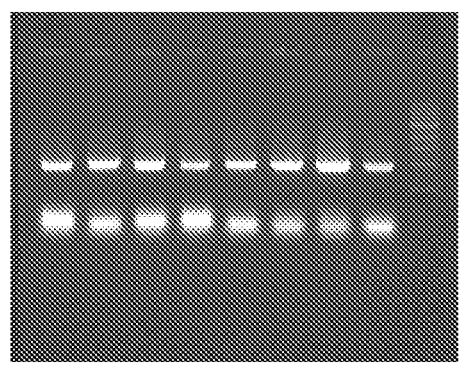
Figure 15:
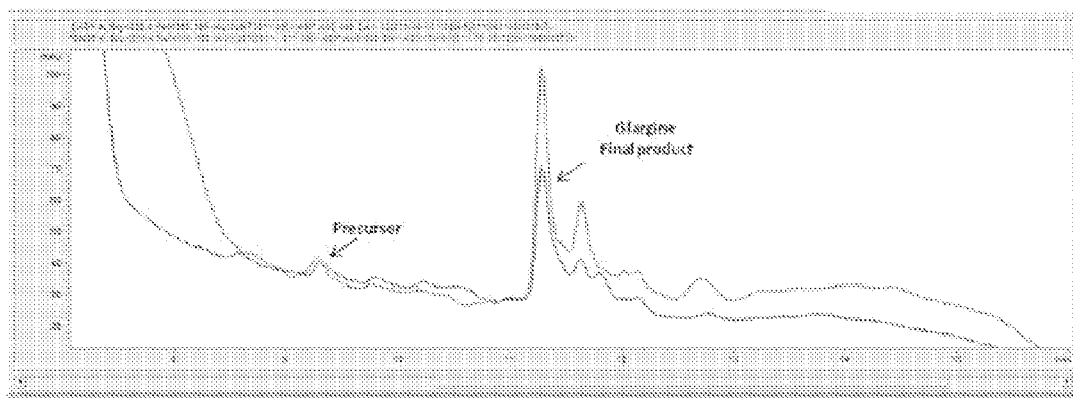

FIG. 14 illustrates the screening of s about 20 clones to confirm the integration. All clones except clone#1, 6, 9 and 13 are given expected PCR amplicon. LaneP is positive control where plasmid was used as a template. Lane 9582 is a negative control (parent strain) and lane M is DNA molecular weight marker FIG. 15 illustrates the typical HPLC profile showing the precursor peak and the two chain glargine peaks. The picture indicated that the conversion is about 90%.

Figure 16:
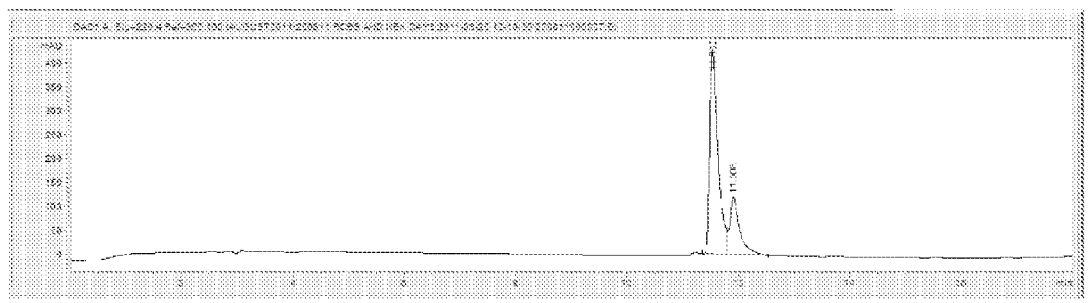

FIG. 16 illustrates HPLC profile of Glargine purified product (2 chain).

Figure 17:
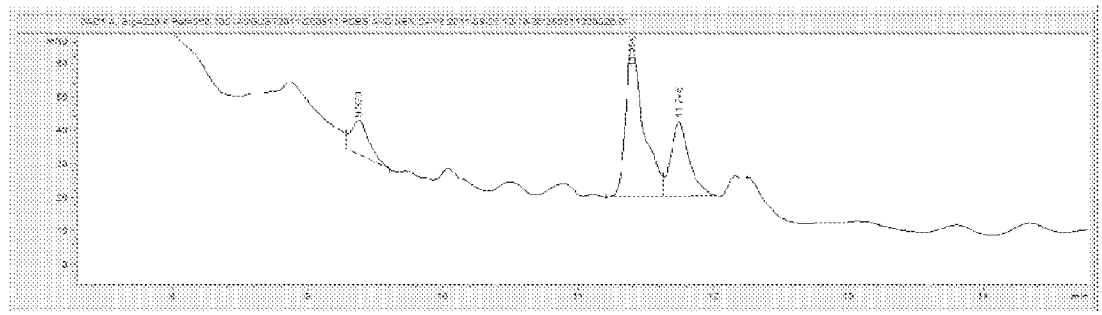

FIG. 17 illustrates HPLC profile of 2 chain Glargine secreted from Kex2 over-expressed clone (FLD-Kex2p).

Figure 18:
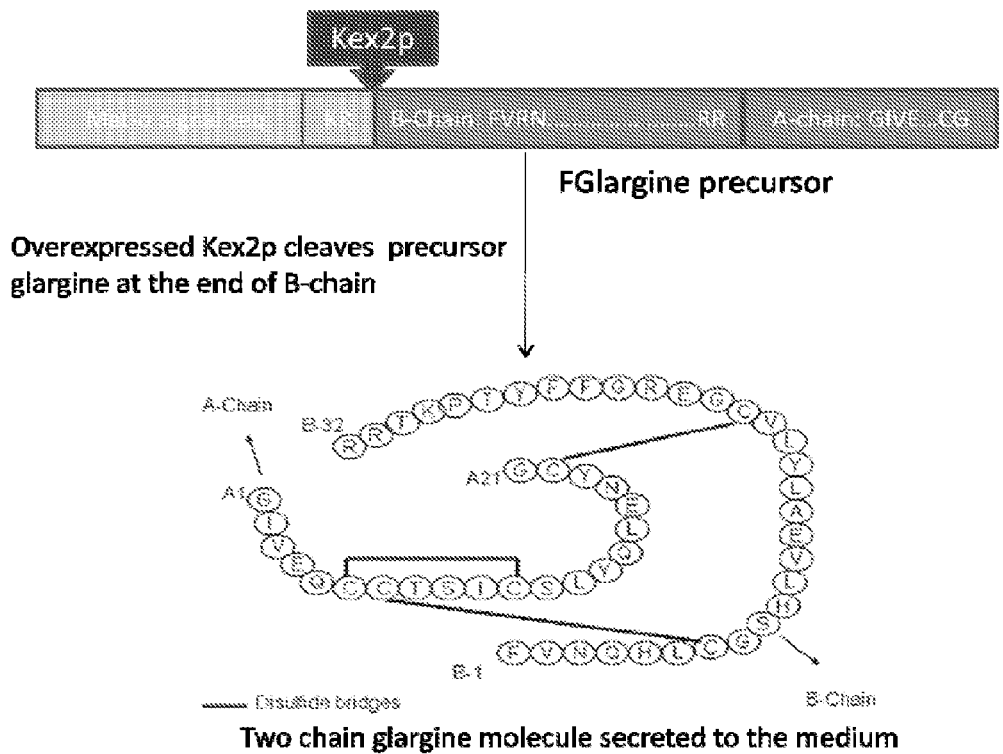

FIG. 18 illustrates the schematic diagram of how the two chains are made inside the host *Pichia pastoris* and secreted into the medium.

Table1 shows the percentage conversion of two chain glargine with co-expression of ΔKex2p under the control of GAP promoter.

Table 2 shows the percentage conversion of two chain glargine with co-expression of ΔKex2p under the control of FLD1 promoter.

DETAILED DESCRIPTION OF DISCLOSURE

The present disclosure is in relation to a process of expressing a fully folded functional two chain insulin glargine that require no further processing to make it functionally active, said process comprising steps of i) cloning a glargine pro-peptide and a protease in *Pichia pastoris* wherein, the sequence coding for protease is put under the control of a constitutive or inducible promoter, ii) co-expressing the said pro-peptide and the protease and iii) obtaining a fully functional insulin glargine.

In an embodiment of the present disclosure, the yield of the fully folded biologically active insulin glargine obtained by the said method is more than 93%.

In still another embodiment of the present disclosure, the glargine pro-peptide is set forth as SEQ ID No. 1.

In still another embodiment of the present disclosure the glargine pro-peptide is set forth as SEQ ID No. 1.

In still another embodiment of the present disclosure the protease is Kexin endoprotease (Kex2p) set forth as SEQ ID No. 2

In still another embodiment of the present disclosure the constitutive promoter is a GAP promoter.

In still another embodiment of the present disclosure the inducible promoter is a FLD1 promoter.

In still another embodiment of the present disclosure the constitutive promoter GAP enables the over expression of Kex2p of SEQ ID No. 2 at levels wherein the protease cleaves the pro-peptide of SEQ ID No. 1 to secrete up to 75% of insulin glargine as a fully folded and functional two chain peptide that requires no further processing to make it active.

In still another embodiment of the present disclosure the inducible promoter FLD1 enables the over expression of Kex2p of SEQ ID No. 2 at levels wherein the protease cleaves the pro-peptide of SEQ ID No. 1 to secrete up to 100% of insulin glargine as a fully folded and functional two chain peptide that requires no further processing to make it active.

The present disclosure also relates to a process of converting pro insulin glargine into fully folded biologically active insulin glargine, said method comprising steps of obtaining a host cell comprising a nucleotide sequence encoding pro insulin glargine and co-expressing Kex2p under the control of FLD1 promoter within the host cell to convert the pro-peptide glargine into a fully folded biologically active insulin glargine.

The present disclosure overcomes the disadvantages associated with the known downstream processes of the prior art have been remedied by over expressing the Kex2p in *Pichia pastoris* to produce two chain functional glargine directly in the medium to avoid the impurities formed due to the Trypsin. The instant disclosure relates to designing an expression system by the co-expressing of Kex2p and FLD1 promoter in *Pichia pastoris* to produce functional glargine into the medium without the use of trypsin.

In another embodiment, the instant disclosure also provides us with the solution to overcome the downstream impurities formed due to the use of serine protease enzyme trypsin by secreting the functional glargine directly in the medium by the over expressing Kex2p intracellularly under the influence of FLD1 promoter. The surprising results of this method is not disclosed in any of the prior art.

However, the present disclosure discloses a process of producing a functional two chain glargine into the medium to enable processing of the insulin glargine into active two chain fully folded form invivo. The surprising effect is due to the over expression of Kex2 in the host cell in presence of FLD1 promoter.

The purpose of the present disclosure is to develop a process of obtaining a fully folded two chain insulin glargine that require no further processing to make it functionally active.

The main objective of the present disclosure is to obtain a fully folded two chain insulin glargine that require no further processing to make it functionally active.

Yet another objective of the present disclosure is to obtain the insulin glargine by co-expressing a pro-peptide of SEQ ID No. 1 and Kex2p in *Pichia pastoris*.

Still another object of the present disclosure is to provide over expressed Kex2p under the control of inducible FLD1 promoter, wherein the inducible promoter FLD1 enables over expression of Kex2p of SEQ ID No. 2 at levels wherein the protease cleaves the pro-peptide to secrete up to 100% of insulin glargine as a fully folded and functional two chain peptide that requires no further processing in the medium.

The present disclosure relates to process of obtaining a fully folded two chain insulin glargine that require no further processing to make it functionally active. The said process comprising steps of:
i) Constructing the insulin Glargine producing clone in *Pichia pastoris;* ii) Synthesis of Insulin glargine (here after Fglargine) coding sequence;
iii) Transformation of *Pichia pastoris*;
iv) Co-expression of FLD1 promoter driven ΔKex2p intracellularly; and
v) Transformation and screening of clones for two chain glargine secretion.

In yet another objective of the present disclosure the insulin glargine is afforded by co-expressing a pro-peptide of SEQ ID No. 1 and Kex2p in *Pichia pastoris*.

Still another object of the present disclosure the Kex2p is over expressed under the control of inducible FLD1 promoter.

In another object of the present disclosure the inducible promoter FLD1 enables over expression of Kex2p at levels wherein the protease cleaves the pro-peptide to secrete up to 100% of insulin glargine as a fully folded and functional two chain peptide that requires no further processing in the medium.

As used herein "insulin analogue" is an insulin molecule having one or more mutations, substitutions, deletions and/or additions of the A and/or B amino acid chains relative to the native human insulin molecule. More specifically, one or more of the amino acid residues may have been exchanged with another amino acid residue and/or one or more amino acid residue may have been deleted and/or one or two amino acid residues may have been added, with the provision that said insulin analog has a sufficient insulin activity. The insulin analogs are preferably such wherein one or more of the naturally occurring amino acid residues, preferably one, two, or three of them, have been substituted by another codable amino acid residue. Examples of insulin analogues are described in the following patents and equivalents thereto: U.S. Pat. No. 5,618,913, EP 254,516, EP 280,534, U.S. Pat. No. 5,750,497 and U.S. Pat. No. 6,011,007. Examples of specific insulin analogues are insulin aspart (i.e., AspB28 human insulin) and insulin lispro (i.e., LysB28, ProB29 human insulin) and "insulin glargine" (Lys B(3), Glu B(29) human insulin.

Trypsin is a typical serine protease and hydrolyzes a protein or a peptide at the carboxyl terminal of an arginine or lysine residue (Enzymes, pp 261-262 (1979), ed. Dixon, M. & Webb, E. C, Longman Group Ltd., London). In particular, facile hydrolysis occurs at a dibasic site where two successive arginine or lysine residues exist, and it is known that hydrolysis occurs most readily where the dibasic site is located in or next to a β-turn structure (Rholam, M., et al., FEBS Lett., 207, I-6 (1986). The Enzyme Vol. II, 3rd Edition, Editor Boyer, Acad. Press NY. Pp. 249-275). Particularly, trypsin cleaves peptide bonds at C-terminal arginine (Arg) or lysine (Lys) residues. Tryptic cleavage of insulin precursor molecules can occur at different cleavage sites simultaneously. Because of the many cleavage sites within a specific insulin precursor molecule, many undesired side-products can be formed during tryptic cleavage reaction.

The present disclosure provides vectors comprising DNA encoding any of the herein described genes. Host cell comprising any such vectors are also provided. By way of example, the host cells may be bacterial, fungal, or mammalian.

The present disclosure employs a recombinant host cell in which at least a portion of a nucleic acid sequence expressing the insulin compound precursor is produced. A recombinant expression system is selected from prokaryotic and eukaryotic hosts. Eukaryotic hosts include yeast cells (e.g., *Saccharomyces cerevisiae* or *Pichia pastoris*), mammalian cells or plant cells. Bacterial and eukaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells. The choice of the expression system depends on the features desired for the expressed polypeptide.

Most preferably related to aspects of the present disclosure, the most preferred host cells are methylotrophic yeasts. Strains of a methylotrophic yeast which can be modified using the present disclosure include, but are not limited to, yeast strains capable of growing on methanol, such as yeasts of the genera *Pichia, Candida, Hansenula*, or *Torulopsis*. Preferred methylotrophic yeasts are of the genus *Pichia*. Methylotrophic yeast strains which can be modified using the present methods also include those methylotrophic yeast strains which have been engineered to express one or more heterologous proteins of interest.

The term "promoter" is used in the normal sense of the art, e.g. an RNA polymerase binding site.

The term "vector" includes expression vectors, replicable vectors, transformation vectors and shuttle vectors, including vector combinations thereof.

The term "expression vector" means a construct capable of in-vivo or in-vitro expression.

Preferably the expression vector is incorporated in the genome of the organism. The term "incorporated" preferably covers stable incorporation into the genome.

In molecular biology, transformation is the genetic alteration of a cell resulting from the direct uptake, incorporation and expression of exogenous genetic material (exogenous DNA) from its surroundings and taken up through the cell membrane(s).

The host cell or organism can be engineered to express recombinant protein or peptide using standard techniques. For example, recombinant protein can be expressed from a vector or from an exogenous gene inserted into the genome of the host.

The expression of the gene encoding the two chain insulin glargine is controlled by a promoter (e.g., an inducible promoter or a constitutive promoter). Preferably, the promoter is a strong promoter, more preferably a strong inducible promoter, which allows for the production of large quantities of the desired product. The cells transformed with the gene may be fungal. For expression in *Pichia pastoris*, the promoter used to drive the expression of the gene is preferably the GAP promoter (a strong constitutive promoter), or the AOX1 or AOX2 promoter (a strong inducible promoter) and the strong FLD1.

Vectors that can be used to express proteins are well known in the art and are described below. Preferred vectors of the present disclosure carrying insulin precursor molecule genes include but are not limited to FLD1-Kex2p/pPICZA.

As used herein the term "expression" refers to a process by which a polypeptide is produced based on the nucleic acid sequence of a gene. The process includes both transcription and translation.

As used herein, the term "primer" refers to an oligonucleotide, whether occurring naturally as in a purified restriction digests or produced synthetically, which is capable of acting as a point of Initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH).

Example 1

Protocols Adapted to Produce Two Chain Insulin Glargine in *Pichia pastoris*

1.1 Constructing the Insulin Glargine Producing Clone in *Pichia pastoris*.

Insulin glargine (here after Fglargine) sequence (SEQ ID No. 1) without the leader sequence is cloned into the *Pichia* expression vector and transformed in *Pichia pastoris*.

Amino acid sequence of the Fglargine sequence SEQ ID No. 1 is as follows:

```
FVNQHLCGSHLVEALYLVCGERGFFYTPKTRRGIVEQCCTSICS
LYQLENYCG
```

Figures 1, 2:
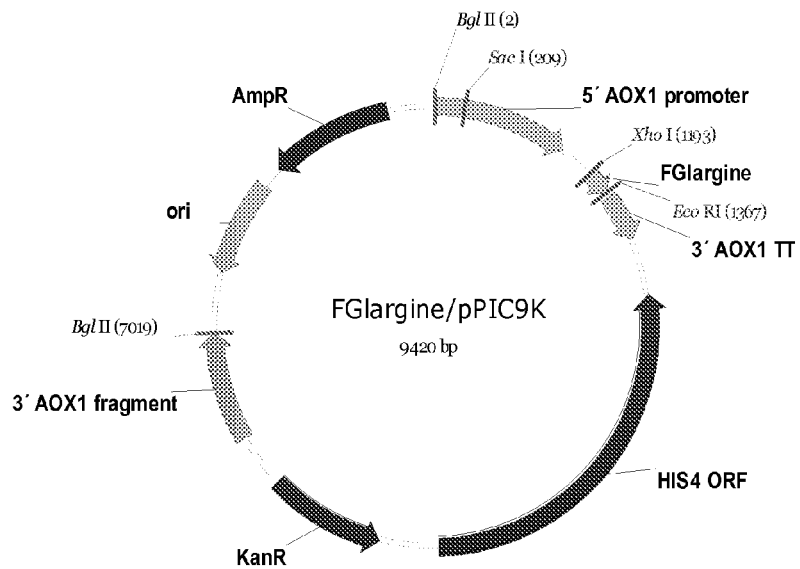
FIG. 1 illustrates the single chain glargine precursor secreting into the medium with black downward arrows showing the trypsin cleavage sites.
FIG. 2 illustrates Vector map of Fglargine/pPIC9K.

1.2 Synthesis of Fglargine Coding Sequence:

The Fglargine coding sequence was codon optimized for expression in *Pichia pastoris* and obtained the synthetic cDNA from Geneart AG, Germany. The desired fragment was amplified with the primers designed specific to the gene and cloned into pTZ57RT vector (Fermentas) and sequence verified. After the sequence integrity was verified, the synthetic Fglargine coding sequence was subcloned into the *Pichia* expression vector in XhoI/EcoRI sites to give Fglargine/pPIC9K (pPIC9K is a plasmid). This cloning step fused the Fglargine coding sequence to the Mat-α signal sequence for secretion and placed it under the control of AOX1 promoter and terminator (as shown in FIG. 2 and SEQ ID No. 1).

Example: 2

Transformation of *Pichia pastoris*

Figure 3:
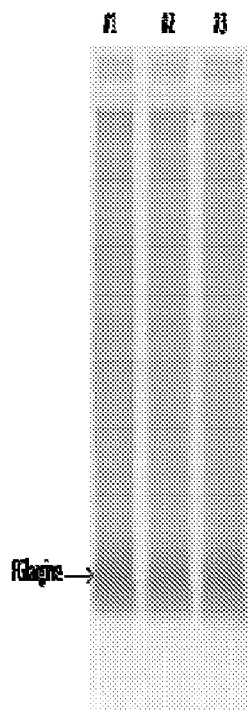
FIG. 3 illustrates the secretion of a single chain of Fglargine using endogenous Kex2p protease. Fglargine #1/GS115 was selected for all the future studies.
Figure 4:
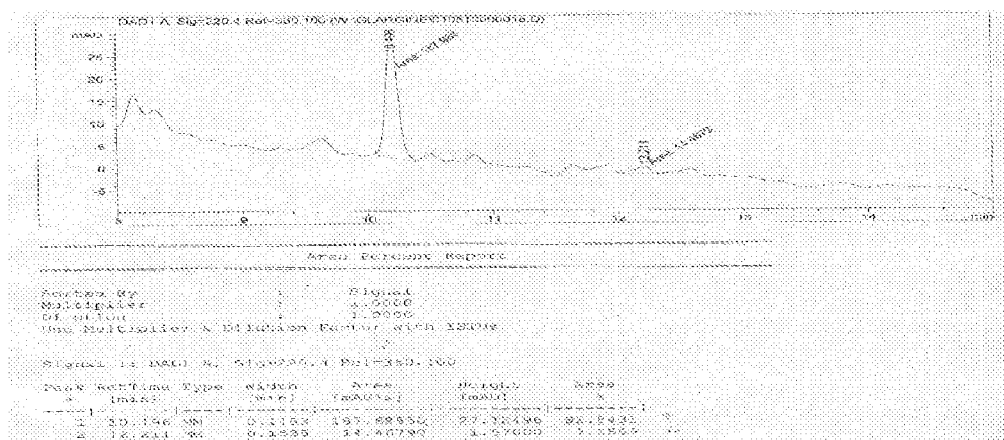
FIG. 4 illustrates mass results of F-glargine in GS115 without kex2p. Only precursor F-glargine is seen.

The construct, Fglargine/pPIC9K was transformed by electroporation into *Pichia pastoris* and selected His phenotypes. Transformation was done by electroporation of freshly grown cells in 0.2 cm cuvettes. The pulse was delivered by Gene Pulser (BioRad) at 1500 V, 25 μF, and 200Ω. The electroporated cells were allowed to recover for 1 hour in 1 M sorbitol at 30° C. and then the transformation mix is spread onto YNBD agar plates. 1200 transformants were screened for integration of multiple copies of Fglargine constructs in the genome by their resistance to successively higher concentrations of G418 (aminoglycoside antibiotic Geneticin). Standard protocols recommended by the manufacturer (Invitrogen Inc.) were followed for screening and expression. The clones chosen on this basis were taken up for expression studies. Fglargine #1/GS115 (selected from the list of 1200 transformants disclosed above) was selected for all the future studies. The productivity of single chain precursor was checked in the shake flask study (FIG. 3) and only precursor Fglargine will be seen without Kex2p (as shown in FIG. 4).

*Pichia pastoris* GS115 is a His⁻ host. It cannot grow in minimal media without amino acid Histidine supplemented. The vector pPIC9K has the His 4 gene. When the vector is transformed to GS115 host the host becomes His⁺. It can grow on minimal media. This is also explained in the *Pichia* expression manual (Invitrogen).

Example: 3

Co-Expression of Kex2p Under the Control of GAP Promoter

From FIG. 4 it is well understood that it is not possible to secrete two chain glargine directly into the medium using endogenous Kex2p alone. Hence attempt to co-express the Kex2p with GAP promoter to increase the protease level endogenously has been taken.

Example: 4

Construction of a Single Copy ΔKex2p Under GAP Promoter

The Kexin endoprotease (Kex2p) is 777 amino acid membranes bound protein. It is very difficult to produce this enzyme by means of recombinant technology. This has the substrate specificity to cleave after di-basic amino acids like RR, KR, KK and RK. The most preferred among the four are KR and RR and it barely clips after RK and KK (see FIG. 5). From the prior art as disclosed in EP0794254A2, only the 660 amino acid cytosolic domain in *S. cerevisiae* is sufficient for the activity. Similarly in the present disclosure Kex2p functional domain of 660 amino acid from the *Pichia* was selected for expression in *Pichia pastoris*. PCR amplification of the gene is carried out corresponding to this functional domain using *Pichia pastoris* genomic DNA as template. The plasmid construct was developed by cloning the 660 amino acid kex2p CDS (here after ΔKex2p) in-frame with GAP promoter without Matα signal peptide for intracellular expression as shown in FIG. 6 and SEQ ID No. 2.

Example: 5

Transformation and Shake Flask Expression Studies

The plasmid ΔKex2p/pGAP is transformed into Fglargine #1/GS115 host using standard protocol. The transformants obtained were screened for Zeocin resistance at the concentration of 0.5 mg/ml (as shown in FIG. 7). Based on the good growth on Zeocin containg plates, following clones were analyzed for the two chain glargine secretion (as shown in FIG. 8). The secretion of two chain is partial and it is about 50 to 60% (as shown in table 1). The Clone #6D6 gives the maximum secretion of two chain of 60%.

Few clones were induced and subjected to HPLC analysis to find out the two chain glargine peaks (as shown in FIG. 9 and FIG. 10). Successful transformation of ΔKex2p/pGAP into Fglargine production host takes place with the conversion or secretion of two chain glargine is varied from about 10% to 60% (as shown in table 1). However, since 100% two chain glargine secretion into the medium was not achieved; a process which increases the secretion of two chain glargine in the medium is required.

TABLE 1

The percentage conversion of two chain glargine with co-expression of ΔKex2p under the control of GAP promoter.

| Clone name/# | Injection volume (μls) | Precursor Peak area | Total peak area | Two chain glargine Peak area | % conversion achieved |
|---|---|---|---|---|---|
| Flargine control | 50.00 | 571.3 | 571.3 | 0.00 | 0.00 |
| Clone #IB4 | 50.00 | 727.9 | 836.9 | 109 | 13.02 |
| Clone #5C5 | 50.00 | 454.9 | 826.5 | 371.6 | 44.96 |
| Clone #3C1 | 50.00 | 403.2 | 588.2 | 185 | 31.45 |
| Clone #4B7 | 50.00 | 485.2 | 731.1 | 245.9 | 33.63 |
| Clone #2F6 | 50.00 | 1386.5 | 1531 | 144.5 | 9.44 |
| Clone# 6D6 | 50.00 | 494.22 | 1221.02 | 726.8 | 59.52 |

Result:
Results from table 2 indicate that the above process successfully transformed the ΔKex2p/pGAP into Fglargine production host. The colonies are screened for obtaining higher Zeocin resistance clones which will lead to high copy number expression construct. The secretion of two chain glargine is varied from about 10% to 60%.

However, we are unable to achieve 100% two chain glargine secretion into the medium.

Example: 6

Co-Expression of FLD1 Promoter Driven ΔKex2p Intracellularly

In order to secrete 100% two chain glargine, co-expression is carried out by ΔKex2p under the control of constitutive GAP promoter. Hence it was also decided to use the strong inducible promoter FLD1 to obtain such high secretion.

Example: 7

Cloning of Kex2p Under the Control of FLD1 Promoter

To secrete 100% two chain glargine directly into the culture medium co-expressing ΔKex2p under the control of FLDI promoter has been carried out.

Procedure:
The FLD1 promoter is a PCR amplified using the following forward primers, FLD (BamH1) FP (5' GCG GAT CCG CAT GCA GGA ATC TCT GGC ACG G 3') and FLD-Kex FP (A5' CAA TTC TTG ATA TTC ACA ATG TAT TTG CCA GCA C 3'). The ΔKex2p was PCR amplified using the following reverse primers FLD-Kex RP (5' GCG AAG TGC TGG CAA ATA CAT TGT GAA TAT CAA GAA 3') and Kex (Sac) RP (5' GGA GCT CGT TTA TGC AAA TAA TGA GAG GGC C 3') (as shown in FIG. 10). These products were gel purified using the gel extraction kit and carried out an overlapping PCR to fuse the product using the primers FLD (BamH1)FP and Kex (Sac)RP.

The Fused PCR product is cloned into pTZ57R vector, Restriction analysis and sequence verification were carried out to confirm the authenticity (as shown in FIG. 11). The restriction digestion analysis and the nucleotide sequences were found to be correct. All the restriction digestion were given the expected fragments (as shown in FIG. 11).

Example: 8

Subcloning FLD1-Kex2p into pPICZA Vector

FLD1-Kex2p was subcloned into pPICZA vector as shown in FIG. 12 and confirmed the same by restriction digestion (as shown in FIG. 13). All the restriction digestion is found to be correct.

Example: 9

Transformation and Screening of Clones for Two Chain Glargine Secretion

The vector FLD1-Kex2p/pPICZA was linearized with BspHI(RcaI) and used for transformation to BICC 9582 which is FGlargine expression host. The transformation was performed by electroporation using Biorad Gene Pulser XL and the transformation mix was selected on YPDS containing 100 µg/ml Zeocin. The plates were incubated at 30° C. for the transformants to appear.

The transformants were screened by colony PCR to find out integration of FLD1-Kex2p in BICC9582 by using primers FLD promoter FP and Kex(Sac)RP. The expected amplicon size was ~975 bps (see FIG. 14). Among the positive clones obtained, clone #5, 7, 23 and 26 were used for evaluation.

Example: 10

HPLC Analysis of the Secreted Fglargine

The selected clones were grown in expansion media to develop cell mass. They were then induced using methanol as per the standard protocol. The samples were analyzed by HPLC to check the two chain glargine secretion as shown in FIG. 15. FLD1 driven Kex2p is able convert >93% of the precursor into fully folded two chain glargine and secrete into the medium as shown in table 2.

TABLE 2

The percentage conversion of two chain glargine with co-expression of ΔKex2p under the control FLD1 promoter. Comparative percentage of yield improvement of two chain insulin-glargine:

| Recombinant insulin-glargine Clone name | % yield increased |
|---|---|
| Insulin-glargine clone without co-expression | 0-5 |
| Insulin-glargine precursor with Kex2p overexpression using GAP promoter | 60 |
| Insulin-glargine precursor with Kex2p overexpression using FLD1 promoter | >93 |

Results:
FLD1 driven Kex2p is able to convert more than 93% of the precursor into fully folded two chain glargine and secrete into the medium.

Example: 11

SDS PAGE Analysis of Two Chain Glargine Clones

The induced samples were analyzed using Tricine SDS PAGE along with controls (as shown in FIG. 15). It is evident from the gel picture that the clones which are co-expressed with FLD1-Kex2p are secreting two chain glargine into the culture medium very efficiently.

We claim:

1. A process of expressing a fully folded functional two chain insulin glargine that requires no further processing to make it functionally active, said process comprising the steps of
   i) cloning a glargine pro-peptide and a protease in *Pichia pastoris*; wherein the sequence coding for the protease is put under the control of a constitutive or inducible promoter and the sequence coding for the glargine pro-peptide is SEQ ID NO: 1;
   ii) co-expressing the pro-peptide and the protease; and
   iii) obtaining a fully functional insulin glargine.

2. The process of claim 1, wherein yield of the fully folded functional insulin glargine obtained by the process is more than 93%.

3. The process of claim 1, wherein the protease is Kexin endoprotease (Kex2p) set forth as SEQ ID NO: 2.

4. The process of claim 1, wherein the constitutive promoter is Glyceraldehyde-3-phosphate dehydrogenase (GAP) promoter.

5. The process of claim 4, wherein the constitutive promoter GAP enables the over expression of Kex2p of SEQ ID NO: 2 at levels wherein the protease cleaves the pro-peptide of SEQ ID NO: to secrete up to 75% of insulin glargine as a fully folded and functional two chain peptide that requires no further processing to make it active.

6. The process of claim 1, wherein the inducible promoter is glutathione-dependent formaldehyde dehydrogenase (FLD1) promoter.

7. The process of claim 6, wherein the inducible promoter FLD1 enables the over expression of Kex2p of SEQ ID NO: 2 at levels wherein the protease cleaves the pro-peptide of SEQ ID NO: 1 to secrete up to 100% of insulin glargine as a fully folded and functional two chain peptide that requires no further processing to make it active.

* * * * *

SEQUENCE LISTING

<160> NUMBER OF SEQ ID NOS: 8

<210> SEQ ID NO 1
<211> LENGTH: 159
<212> TYPE: DNA
<213> ORGANISM: Artificial Sequence

```
<220> FEATURE:
<223> OTHER INFORMATION: A synthetic oligonucleotide
<220> FEATURE:
<221> NAME/KEY: gene
<222> LOCATION: (1)..(159)

<400> SEQUENCE: 1
tttgttaacc aacatttgtg tggttctcat ttggttgaag ctttgtactt ggtttgtggt      60
gaaagaggtt ttttttacac tccaaagact agaagaggta ttgttgaaca atgttgtact     120
tctatttgtt ctttgtacca attggaaaac tactgtggt                            159

<210> SEQ ID NO 2
<211> LENGTH: 1983
<212> TYPE: DNA
<213> ORGANISM: Pichia pastoris
<220> FEATURE:
<221> NAME/KEY: Sequence of truncated Kex2P
<222> LOCATION: (1)..(1983)

<400> SEQUENCE: 2
atgtatttgc cagcacttcg cttagcatgc tggatcttaa ttggtcttag gtctacggag      60
gctttggaga cttccgagag agagatcttt gctctcaagc tggataaatc ctggcttcca     120
acgtttctag aaacgttcca agataagttc aggtatgaaa gacagatcaa cggtttggat     180
gactaccatg ttttttcaca cagtaagaac gaagagtttc agttagagaa ctttaaagtg     240
aagactcttt tgacgcgaga caacgccaat cttcactccg aactgatttc ccacaatgtg     300
gacgaggttc acatgctaag gccctctcat tatttgcata acgagctccc tgttgtgatg     360
gacaagtcag aggaattaag agaacaaata gcgaaggatt ttgacattga tgaccccttta    420 tttgctaaac agtggcatct atttaatcct cgttacccag acacgacgt gaacgtgtcg     480 caagtttggt acgatggtat cactggaaaa ggtgtagtga ccgccatagt tgatgacgga     540
ctagatatgg acagtaaaga tctcaaagaa tcttttttgtg aggaaggatc ttgggatttc    600
aatgccaaca ctagactacc caaaccaaga cttagagacg atcaccacgg aaccagatgt     660
gcagcggaga ttgcagctaa aagggaaat aaatactgtg gagttggtgt ggcatatgat     720
tcaaaggttt ctggcatcag gattcttagt gataaaatca caccagagga tgaagctctc    780
tccttaatct acggtcttga tgtcaacgac atttattcat gttcatgggg gccagcagac     840
aatggaatca caatgcaagg tcccagctcg ttagtcaaag aagccatgct taaaggagtt     900
caggatggaa gaaagggtaa aggtgcgctg tatgtattcg ccagtggaaa cggagcatct    960
tctggtgata actgcaattt tgacgggtac accaatagca tttattccat aacagttggg    1020
gcaattgata ttaaagggct tcatccacca tacgctgagg cttgctctgc tgtgatgact    1080
gtcacataca gttctggatc gggtgagcac atacacacaa ccgacatcaa cgataaatgt   1140
tctgataccc atggaggaac atccgctgct gcacctttag cggctggtct ttattctttg   1200
gtttatcagg ctaatccgga cctgacttgg cgagatattc aatggctgac tgttttaaca   1260
gccgttcctg ttaacgaaca ggagcctggc tggcagaaga ctgctatcgg taagatgtat   1320
tctcataaat acggatatgg caagatcgat gcatatgcac tggtcaatct agcaagatct   1380
ccagacttcc cgtatctcaa accacaaagc tggatttatg cactgaggt tcacgaaagc   1440 ttgaatactt ccgaagctaa cggtgtgctg acatccaagt atgaattgac ccaggaggcc   1500
aaagatctaa tgaactttga aaaaattgag catgttacgg ttactgtaga tataaaggcg   1560
gcggaaagag gtaaagttct tgttgagttg atctccccct caggtgttgt cagtgaattg   1620
```

| | |
|---|---|
| gctccctatc gaagaatgga caaggataag gaaggatttc caaattggac gttcatgtca | 1680 |
| gtagctcatt ggggtgaaga cgggttagga gagtggatat tgaaaatcac taacaaagaa | 1740 |
| ggaaattctg tggtgcttaa ctcctggcaa ataaaattct ttggagaaag tcaagaccct | 1800 |
| gaaaaggctg aaaaattctc tttaactaag aaatatgacg aaatattagt caaccctcca | 1860 |
| tcttcatcta cttccacgac agtggacacc tcatctacag aagccacttt ttcgtcttcc | 1920 |
| tctgttttcag aggcttcagc cacggaaacg gatgtaaaag agacttctac aaccggtgat | 1980 |
| taa | 1983 |

<210> SEQ ID NO 3
<211> LENGTH: 603
<212> TYPE: DNA
<213> ORGANISM: Pichia pastoris
<220> FEATURE:
<221> NAME/KEY: promoter
<222> LOCATION: (1)..(603)

<400> SEQUENCE: 3

| | |
|---|---|
| ggatccgcat gcaggaatct ctggcacggt gctaatggta gttatccaac ggagctgagg | 60 |
| tagtcgatat atctggatat gccgcctata ggataaaaac aggagagggt gaaccttgct | 120 |
| tatggctact agattgttct tgtactctga attctcatta tgggaaacta aactaatctc | 180 |
| atctgtgtgt tgcagtacta ttgaatcgtt gtagtatcta cctggagggc attccatgaa | 240 |
| ttagtgagat aacagagttg ggtaactaga gagaataata gacgtatgca tgattactac | 300 |
| acaacggatg tcgcactctt tccttagtta aaactatcat ccaatcacaa gatgcgggct | 360 |
| ggaaagactt gctcccgaag gataatcttc tgcttctatc tcccttcctc atatggtttc | 420 |
| gcagggctca tgccccttct tccttcgaac tgcccgatga ggaagtcctt agcctatcaa | 480 |
| agaattcggg accatcatcg attttagag ccttacctga tcgcaatcag gatttcacta | 540 |
| ctcatataaa tacatcgctc aaagctccaa cttttgcttgt tcatacaatt cttgatattc | 600 |
| aca | 603 |

<210> SEQ ID NO 4
<211> LENGTH: 483
<212> TYPE: DNA
<213> ORGANISM: Pichia pastoris
<220> FEATURE:
<221> NAME/KEY: promoter
<222> LOCATION: (1)..(483)

<400> SEQUENCE: 4

| | |
|---|---|
| agatcttttt tgtagaaatg tcttggtgtc ctcgtccaat caggtagcca tctctgaaat | 60 |
| atctggctcc gttgcaactc cgaacgacct gctggcaacg taaaattctc cggggtaaaa | 120 |
| cttaaatgtg gagtaatgga accagaaacg tctcttccct tctctctcct tccaccgccc | 180 |
| gttaccgtcc ctaggaaatt ttactctgct ggagagcttc ttctacggcc cccttgcagc | 240 |
| aatgctcttc ccagcattac gttgcgggta aaacggaggt cgtgtacccg acctagcagc | 300 |
| ccagggatgg aaaagtcccg gccgtcgctg gcaataatag cgggcggacg catgtcatga | 360 |
| gattattgga aaccaccaga atcgaatata aaaggcgaac acctttccca attttggttt | 420 |
| ctcctgaccc aaagacttta aatttaattt atttgtccct atttcaatca attgaacaac | 480 |
| tat | 483 |

<210> SEQ ID NO 5
<211> LENGTH: 31

-continued

```
<212> TYPE: DNA
<213> ORGANISM: Pichia pastoris
<220> FEATURE:
<221> NAME/KEY: primer_bind
<222> LOCATION: (1)..(31)

<400> SEQUENCE: 5
gcggatccgc atgcaggaat ctctggcacg g                               31

<210> SEQ ID NO 6
<211> LENGTH: 36
<212> TYPE: DNA
<213> ORGANISM: Pichia pastoris
<220> FEATURE:
<221> NAME/KEY: primer_bind
<222> LOCATION: (1)..(36)

<400> SEQUENCE: 6
gcgaagtgct ggcaaataca ttgtgaatat caagaa                          36

<210> SEQ ID NO 7
<211> LENGTH: 34
<212> TYPE: DNA
<213> ORGANISM: Pichia pastoris
<220> FEATURE:
<221> NAME/KEY: primer_bind
<222> LOCATION: (1)..(34)

<400> SEQUENCE: 7
caattcttga tattcacaat gtatttgcca gcac                            34

<210> SEQ ID NO 8
<211> LENGTH: 31
<212> TYPE: DNA
<213> ORGANISM: Pichia pastoris
<220> FEATURE:
<221> NAME/KEY: primer_bind
<222> LOCATION: (1)..(31)

<400> SEQUENCE: 8
ggagctcgtt tatgcaaata atgagagggc c                               31
```